United States Patent [19]

Messenger

[11] Patent Number: 6,020,327

[45] Date of Patent: Feb. 1, 2000

[54] CONTROL OF HAIR GROWTH

[75] Inventor: Andrew Guy Messenger, Sheffield, United Kingdom

[73] Assignees: The Central Sheffield University Hospitals NHS Trust, Sheffield; Bio-Scientific Ltd, London, both of United Kingdom

[21] Appl. No.: 08/809,135

[22] PCT Filed: Sep. 13, 1995

[86] PCT No.: PCT/GB95/02166

§ 371 Date: Mar. 14, 1997

§ 102(e) Date: Mar. 14, 1997

[87] PCT Pub. No.: WO96/08231

PCT Pub. Date: Mar. 21, 1998

[30] Foreign Application Priority Data

Sep. 14, 1994 [GB] United Kingdom .................. 9418484
Sep. 15, 1994 [GB] United Kingdom .................. 9418547

[51] Int. Cl.$^7$ ...................... A61K 31/565; A61K 31/445; A61K 31/41
[52] U.S. Cl. .......................... 514/170; 514/177; 514/178; 514/318; 514/328; 514/383; 514/387; 514/766
[58] Field of Search ...................... 514/177, 170, 514/178, 318, 328, 383, 387, 766

[56] References Cited

U.S. PATENT DOCUMENTS 4,684,635  8/1987  Orentreich et al. ..................... 514/170
5,053,403  10/1991  Orentreich et al. ..................... 514/170

FOREIGN PATENT DOCUMENTS

| | | |
|---|---|---|
| 0163490 | 12/1985 | European Pat. Off. . |
| 0566979 | 10/1993 | European Pat. Off. . |
| 2840144 | 3/1980 | Germany . |
| 3615396 | 11/1987 | Germany . |
| 3621757 | 1/1988 | Germany . |
| 61-18711 | 1/1986 | Japan . |
| 62-103005 | 5/1987 | Japan . |
| WO 85/02543 | 6/1985 | WIPO . |
| WO 86/01402 | 3/1986 | WIPO . |
| WO 86/02269 | 4/1986 | WIPO . |

OTHER PUBLICATIONS

Ebling et al. (1982) J. Steroid Biochem. 83:587–90.
Schweikert, H.U. (1972) J. Clin. Endocrinol. Metab. 74:1012–9.
Schweikert et al. (1972) J. Clin. Endocrinol. Metab. 74:811–9.
Jenkins et al. (1973) J. Endocrinol. 73:345–51.
Sawaya, M.E. (1991) Ann. NY Acad. Sci.:376–84.
Brodie, A.M.H. (1993) Pharmacol. Ther. 60:501–4.
Dowsett et al., Cancer Chemother. Pharmcol., 27(1), 67–71 (abstract), 1990.

*Primary Examiner*—Phyllis G. Spivack
*Attorney, Agent, or Firm*—Klauber & Jackson

[57] ABSTRACT

A method for treating hair loss is disclosed by topically adminstering an aromatase inhibitor to a mammal, including humans, on the area to be treated.

10 Claims, No Drawings

CONTROL OF HAIR GROWTH

FIELD OF THE INVENTION

The present invention relates to a method for determining the predisposition to hair loss and to preparations for the regulation of hair growth. These preparations are particularly applicable to the treatment of hair regression on the scalp and baldness and to depilatory agents in mammals, including humans.

BACKGROUND TO THE INVENTION

Hirsuties and female androgenetic alopecia are common androgen-dependent problems. For example, each year about 200 women with these conditions are referred to the Department of Dermatology in Sheffield; patients are also referred to endocrinologists and gynaecologists. Hair is an important cosmetic asset and although these conditions are not physically disabling they can have a profound adverse affect on the quality of life. Current treatments for hirsuties are, at best, only modestly effective. There is no worthwhile treatment for female androgenetic alopecia and, in most cases, management is limited to ensuring that there is no serious endocrine pathology and prescribing a wig for severely affected patients. Better treatments are needed but their development is hampered by our poor understanding of the basic biology. In particular, we do not understand why androgens stimulate hair growth over most of the skin but inhibit hair growth on the scalp.

Balding is a common alteration in the pattern of scalp hair growth. It affects both men and women although the degree of hair loss is less and tends to occur in a more diffuse pattern in women. Genetic factors are thought to be important and there are racial differences in the prevalence. There is strong evidence that androgen hormones are necessary for the development of balding but the mode of hormone action on the hair follicle is unknown. At present there is no satisfactory treatment. However, the following have some proven benefit;

Minoxidil

Topical application of minoxidil produces modest recovery in early balding in about 30% of subjects. Minoxidil is a potassium channel agonist in vascular smooth muscle. A number of other potassium channel agonists have been reported to stimulate hair growth (e.g diazoxide, nicorandil) suggesting that this pharamacological property is relevant to their hypertrichotic effect. However the mechanism of action is unknown.

Cyproterone Acetate (CPA)

This is a steroidal androgen receptor blocker which also has progestational activity. Several small trials indicate a small positive affect in female hair loss. CPA has to be taken orally and therefore cannot be used in men (whom it would feminize). There are no topical formulations available as far as we know.

Hair Surgery eg. hair transplantation, scalp reduction.

These techniques are not readily available and have very limited applications. Numerous other products have been promoted for the treatment of balding but, other than those listed above, there is no adequate clinical data on the results.

Development of new effective treatments for balding has been limited by our poor understanding of the basic biology, and the absence of suitable animal models for the routine testing of compounds.

Biological Background

Androgen hormones (e.g testosterone) are the major systemic influence on hair growth in man. In most body sites, such as the beard and pubic skin, androgens stimulate hair growth by prolonging the growth phase of the hair cycle (anagen) and increasing follicle size. Hair growth on the scalp does not require androgens but, paradoxically, androgens are necessary for balding on the scalp in genetically predisposed individuals (androgenetic alopecia) where there is a progressive decline in the duration of anagen and in hair follicle size. Men castrated before puberty fail to grow beards and do not go bald. If subsequently treated with testosterone about one third of male castrates will show balding (1). Androgenetic alopecia is also common in women where it usually present as a diffuse hair loss rather than showing the patterning seen in men.

Current thinking is that testosterone is necessary for the development of balding but as only a proportion of men show balding, and there is no difference in circulating testosterone levels between bald and non-bald men, other factors must be needed for hair loss to occur. Until this work was carried out there was little indication as to what these other factors might be. Further evidence implicating androgens in balding (and growth of beard and body hair) is that genetic males who lack intracellular androgen receptors [testicular feminization] fail to grow body hair and do not go bald in spite of high circulating levels of testosterone. It is generally believed that in most body sites, testosterone is metabolised in the skin to the potent androgen dihydrotestosterone (DHT) by the enzyme 5α-reductase before acting on hair growth. There is considerable literature relating to the involvement of DHT in hair loss in both males and females (WO-A-8 502 543, WO-A-8 602 269, EP-A-0 566 979, EP-A-0 163 490, WO-A-8 601 402, DE-A-2 840 144, U.S. Pat. No. 4,684,635, J. Steroid Biochem. Vol. 19, no. 1, pp. 587–590, 1983, JCE and M, Vol. 39, no. 6, pp. 1012–1019, 1974, JCE and M, Vol. 38, no. 5, pp. 811–819, 1974 J. Endocr., Vol. 59, no. 2, pp. 345–351, 1973 J. Cutan Pathol 1991: 19: 309–314 and M. E. Sawaya: Steroid Chemistry and Hormone Control during the Hair Follicle Cycle, pages 377 to 384). Genetic males with type 2 5α-reductase deficiency have normal or raised circulating testosterone levels but show a female pattern of body hair and sparse or absent beard growth. It is said that men with type 2 5α-reductase deficiency do not go bald but the evidence implicating this metabolic pathway in balding is less clear cut. Nothing is known of the prevalence of balding in the normal populations in which these cases have been reported and studies to date have failed to demonstrate the type 2 form of 5α-reductase in normal scalp. Administration of 5α-reductase inhibitors in macaques, a primate species which undergoes androgen-dependent scalp hair loss, has been reported to prevent and partially reverse the balding process but there is no clinical trial data published in humans. If DHT is involved in balding it would appear that the effect is derived from circulating DHT, not DHT synthesised in the scalp. This fails to explain why only a proportion of men show balding characteristics.

Hair is a keratinized differentiation product of a highly proliferative population of epithelial cells situated at the base of the hair follicle (the hair bulb matrix). Hair is not produced continuously; individual hair follicles undergo a repetitive sequence of growth (anagen) and rest (telogen) known as the hair cycle. Control of the hair cycle is determined primarily within the hair follicle itself but this intrinsic behaviour can be modulated by systemic influences mainly mediated by the endocrine system (2). The hair follicle also contains a dermal component derived from embryonic mesenchyme. This comprises the dermal sheath surrounding the follicle and the dermal papilla which invaginates the base of the hair bulb. Transplantation studies in rodents have shown the dermal papilla plays a vital role in hair growth. It is responsible for inducing growth and differentiation of follicular epithelium. It determines the follicle type (whisker, pelage etc.) and probably the diameter of the hair and there is indirect evidence that the dermal papilla is responsible for regulating the hair cycle (3,4). A number of studies have suggested that, in follicles where androgens stimulate hair growth, the hormone acts primarily on the dermal papilla. Dermal papilla cells cultured from human hair follicles express saturable, high affinity androgen receptors and the receptor concentration is higher in cells from beard follicles than from occipital scalp follicles (a relatively non-androgen responsive site) (5). Androgen receptors have also been demonstrated in the nuclei of dermal papilla cells in tissue sections by immunohistochemistry using a specific monoclonal antibody (6). Significantly, there was no antibody staining of cells in the epithelial compartment of the hair bulb. Dermal papilla cells cultured from beard follicles also express type 2 $5\alpha$-reductase whereas those from scalp follicles do not (7). Type 1 $5\alpha$-reductase is present in the scalp but men with $5\alpha$-reductase deficiency have normal levels of this enzyme. Therefore it seems likely that androgen action on the beard is mediated by DHT acting primarily on the dermal papilla but it is difficult to explain the inhibitory affect of androgens on scalp hair growth on the same basis.

In conclusion, the prior art is confusing in that it fails to explain the observed pattern of hair loss in a proportion of the population. It also provides no reasonable hypothesis on which to either predict a pre-disposition to hair loss and little basis upon which to base a systematic search for new and improved treatments.

Our investigations have instead lead us to study in some detail aromatase, a cytochrome p450 enzyme which catalyses the metabolism of androstenedione and testosterone to estrone and oestradiol respectively. It is localized mainly in the ovary and the placenta and participates in the regulation of reproductive functions. Aromatase activity is also found in extra-gonadal tissues such brain, liver adipose tissue and genital skin fibroblasts. The aromatase pathway of androgen metabolism has received scant interest in hair biology and little is known about the effect of estrogens on human hair growth. However a number of lines of evidence suggested to us that it may be important:

In all mammalian species to have been studied (various rodents, dogs), estrogens inhibit hair growth (8).

Aromatase activity has been detected in plucked human scalp hair follicles (9).

Aromatase protein has been detected in human scalp follicles by immunochemistry (10).

We have recently found evidence of aromatase activity in vivo in rat hair follicles. This was an incidental finding in a study designed to measure the effect of a novel pre-estrogenic steroid on sebaceous secretion. The compound in question is metabolized to estrogen by the action of aromatase and will only act as an estrogen in tissues which possess estrogen receptors and aromatase activity. Topical application inhibited hair growth in the rat by about 35%.

In genital skin fibroblasts, aromatase activity is stimulated by testosterone via an androgen receptor mediated mechanism (11).

As a result we formulated the following hypothesis:

In hair follicles in most body sites, testosterone acts as a pre-hormone and the response to testosterone is determined by which metabolic pathway predominates. In skin sites where $5\alpha$-reductase activity is high, such as in the beard, testosterone is metabolised to DHT which has a stimulatory action on hair growth. In scalp, testosterone is metabolised mainly via the aromatase pathway to estrogens causing inhibition of hair growth. Aromatase activity is under receptor-mediated androgenic control; hence balding does not occur in testicular feminisation. The greater severity of balding in men compared with women can be explained by higher levels of oestrogen being attained in the male scalp by virtue of androgen stimulated aromatase activity. An analogous situation exists in the brain where certain aspects of male behaviours in a number of avian and mammalian species are determined by oestrogens synthesised locally by androgen-dependent aromatisation of androgens (12). This hypothesis is also able to encompass a role for $5\alpha$-reductase; as DHT is a more potent androgen than testosterone, circulating or locally formed DHT can be a more effective inducer of aromatase.

SUMMARY OF THE INVENTION

In its broadest aspect, the invention concerns the realisation that aromatase, and more specifically androgenically controlled aromatase, has a role to play in hair loss.

According to a first aspect of the invention there is therefore provided the use of an aromatase inhibitor as a cosmetic agent.

According to a second aspect of the invention there is provided a cosmetic method for treating or preventing hair loss comprising administering an aromatase inhibitor to an area to be treated.

In a preferred embodiment of this aspect of the invention the aromatase inhibitor comprises any one or more of the inhibitors listed herein; aminoglutethimide, 4-OH androstenedione, 6-hydroximino-androstenedione, 9,10-dimethyl 1,2-benzanthracene, 1,4,6-androstatrien-3,17-dione, atamestane, exemstane, fadrozole, vorozole, 1,2,4-triazole-3-alanine and rogletimide. Alternatively the aromatase inhibitor may comprise an antibody raised against at least a part of said aromatase enzyme. The antibody may be polyclonal or monoclonal, monoclonal antibodies are preferred because of their homogeneity, however polyclonal antibodies are more easily produced by injection of a suitable laboratory animal with at least a part of the enzyme and subsequently collecting serum therefrom and isolating specific sera using known techniques. Alternatively, monoclonal antibodies may also be produced using techniques well know to those skilled in the art.

According to a third aspect of the invention there is provided an antibody raised against the enzyme aromatase. Ideally the antibody is for use in preventing hair loss in cosmetic procedures.

According to the fourth aspect of the present invention, there is provided the use of an aromatase inhibitor in the manufacture of a preparation for the reduction in the regression of hair growth or in the alleviation of baldness. Such preparations induce, maintain or increase hair growth and can reverse, arrest or prevent the onset of baldness.

Preferably, the preparation is formulated for topical application with suitable excipients in the form of a lotion.

Alternatively, the preparation may take the form of a cream, shampoo, conditioner or spray.

Preferably, the aromatase inhibitor is selected because it is readily absorbed from the preparation into the skin and into the appropriate skin cells. One means to achieve this is to use an aromatase inhibitor with lipophilic properties. One example of such an inhibitor is 4-hydroxy androstenedione. In principle any known or novel aromatase inhibitor can be used in such a formulation.

According to a fifth aspect of the invention, there is provided the use of an agent adapted to selectively bind to an androgenic receptor, such that receptor mediated androgenic control of aromatase is suppressed or prevented, as a cosmetic agent.

In a preferred embodiment of this aspect of the invention, said agent is an antagonist able to bind to said receptor but unable to produce a receptor mediated response.

Preferably, the antagonistic agent may be synthetically produced or naturally occurring or alternatively a manipulated form of the naturally occurring androgen, for example, it may comprise a form of the naturally occurring androgen which is able to bind, and so block, the relevant receptor but unable to produce a receptor mediated response.

According to a sixth aspect of the invention, there is provided a medicament and/or cosmetic agent comprising an aromatase inhibitor and an androgen receptor antagonist.

In a preferred form of this aspect of the invention, the aromatase inhibitor and the androgen receptor antagonist will be provided in a ratio that is related to the cellular concentrations of the corresponding aromatase and receptor.

Preferably, said inhibitor is an antibody, polyclonal or monoclonal, which has been raised against a part of the aromatase enzyme.

According to an seventh aspect of the invention, there is provided a cosmetic method for treating or preventing hair loss comprising administering, either successively or simultaneously, an aromatase inhibitor and an androgenic receptor antagonist.

In a preferred method of the invention said aromatase inhibitor is any one or more of the inhibitors listed herein, such as, for example, 4-OH androstenedione Preferably, the said androgenic receptor antagonist is for example, cyproterone acetate.

According to a eighth aspect of the present invention, there is provided a cosmetic method of detecting if an individual is predisposed to hair growth regression or baldness by taking a sample of cells from various skin sites prone to baldness on the individual, culturing these cells, measuring their aromatase activity and comparing this activity with control values for people within a control group and values from people who have suffered from hair loss.

According to a ninth aspect of the present invention, there is provided afore method for detecting whether an individual is likely to benefit from treatment with an aromatase inhibitor preparation. It is possible that only a proportion of those presenting at clinic will respond to such treatment because aromatase activity may not be the only mechanism responsible for hair loss. This detection of abnormal levels of aromatase activity may indicate that this form of treatment is likely to be successful or worthwhile.

Description

If the above hypothesis is correct, we would expect the following:

There will be a higher level of aromatase activity in skin sites prone to balding i.e frontal scalp and vertex than in non-balding sites such as the occipital scalp and the beard.

Skin aromatase activity will be induced by androgens via the androgen receptor.

In a preliminary study to investigate the above hypothesis we have measured aromatase activity in cultured human hair follicle dermal papilla cell lines and non-follicular skin fibroblasts from body sites with different responses to androgens. Aromatase was measured using the tritiated water released assay (13). The results are summarised as follows:

Skin fibroblast lines from beard (N=5,) occipital scalp (N=5) and frontal scalp (N=7) all possessed aromatase activity. Enzymic kinetic values were established by incubating cells with the substrate (androstenedione) in a range of concentrations. The highest activities were found in cell lines from the frontal scalp i.e from a potentially balding site. Mean $V_{max}$ (fmol/mg protein/hour)+/− SEM in beard, occipital and frontal cells were 892+/−155, 914+/−188 and 2,817+/−866 respectively. There was no difference in the Km for androstenedione (mean=25 nmol) between the three sites. This value is similar to that quoted for other tissues.

Fibroblast aromatase was stimulated by pre-incubating cells with testosterone at physiological concentrations (10 nmol). 19 cell lines were studied. Mean fold increase in aromatase activity (+/− SEM) was 2.69+/−0.38 (p<0.02 paired test). In separate experiments on three cell lines the response to a range of concentrations of testosterone and DHT was studied. Testosterone gave a twofold increase in aromatase maximal at 10 nmol. At the same concentration in response to DHT was over twice as great (4.3 fold). This response to testosterone DHT was inhibited by cyproterone acetate (which blocks androgen receptors) indicating that androgen stimulation of skin aromatase is via an androgen receptor dependent mechanism.

No aromatase was detected in hair follicle dermal papilla cells cultured through any of the above sites (fourteen cell lines). Testosterone failed to induce aromatase in dermal papilla cells.

Dexamethasone stimulated aromatase 10–20 fold in fibroblasts (six cell lines) and induced aromatase in dermal papilla cells (four cell lines).

Fibroblast aromatase was inhibited by 4-OH androstenedione, a known inhibitor of aromatase in other tissues. Kinetic studies in three cell lines were consistent with irreversible competitive inhibition. 50% inhibition occurred at approximately 25 nmol concentration.

Current thinking is that androgens are acting on the Dermal Papilla. The observation that there was no detectable aromatase activity in hair follicle dermal papilla cells would point away from our hypothesis. In contrast to the established line of thinking we believe that aromatase activity in non-follicular skin fibroblasts is more important and could account for the change in skin texture seen in balding sites.

The high levels of aromatase in fibroblasts from frontal scalp is consistent with our original hypothesis. The putative inhibitory effect of oestrogens on hair growth would need to derive from the surrounding dermis as aromatase activity was absent in dermal papilla cells. There is no evidence that androgens act directly on the hair follicle in the balding process and subjective observation of a balding scalp suggests that there is a general alteration in skin texture. It is possible therefore that inhibition of hair growth is a secondary response to more general changes in local biology of the skin.

The response to testosterone and its inhibition by androgen receptor blockade is consistent with the absence of balding in testicular immunisation. DHT is a more potent inducer of aromatase than testosterone and this may explain the claimed absence of balding in 5α-reductase deficiency. The absence of aromatase in dermal papilla cells when there are high levels in skin fibroblasts from the same tissue sample was a surprise finding and is the first evidence of a qualitative biochemical difference between these two cell types. The dissimilar response of dermal papilla cells and fibroblasts to testosterone and dexomethasone also suggests that aromatase is regulated differently in these two cell types. Tissue specific regulation of aromatase is well recognised (14, 15) and probably occurs at the of level gene transcription although non-genomic regulation has also been described in avian brain. These findings suggest that absence of aromatase activity is an important feature of dermal papilla function and that the maintenance of a "low oestrogen" environment may be necessary for hair growth to proceed.

It thus follows that treatment with an aromatase inhibitor will reduce or eliminate conversion of testosterone to oestrogen and consequently slow down or even reverse the balding process. The aromatase inhibitor can be formulated in a variety of ways. Although systemic administration is possible it is anticipated that side effects will be minimised by topical application. This can be achieved by way of a lotion or cream, including the usual excipients, creme base, stabilisers etc, or by way of a shampoo, conditioner, or spray. Such formulations are well-know to pharmacists skilled in the art and need no further detailing at this point.

Alternatively, by measuring the aromatase activity in cultured skin cells from a particularly individual and comparing this activity with control values from people with a full head of hair and values from people who have suffered hair loss, it is possible to determine if an individual is predisposed to hair growth regression or baldness.

It is also possible to use a combination of two or more aromatase inhibitors in the same preparation in order to maximise its activity. Such inhibitors may be specifically designed for the purpose or may be chosen from the non-comprehensive list of known inhibitors given below;

In summary the preparations described above induce, maintain or increase hair growth and reverse, arrest or prevent the onset of baldness. They may thus be particularly applicable to people pre-disposed to such conditions.

It will be appreciated that if the aromatase enzyme is important in the regulation of certain aspects of hair growth, it is also possible to increase estrogen concentrations and thus reduce hair growth, by treatment with a pre-oestrogen. Such compounds are known to those skilled in the art and can be formulated for topical application using suitable conventional means. They are converted in vivo to estrogen which can then exert its known effects on the hair cycle.

Topical application of a pre-estrogen is particularly usual for the treatment of hirsutism and as a depilatory agent. Again, assaying the skin cells for the presence of aromatase activity can give a prior indication that such treatment is likely to be effective.

Preferably, the aromatase inhibitor or other active component is in substantially pure pharmaceutical form. Administration may be by any suitable route but the transdermal route is preferred. Topical preparations may be in the form of a cream, shampoo, conditioner or spray.

Liquid preparations may be in the form of, for example, aqueous or oily suspensions, solutions, emulsions, or may be presented as a dry product for reconstitution with water or other suitable vehicle before use. Such liquid preparations may contain conventional additives such as suspending agents, emulsifying agents, non-aqueous vehicles and, if desired, conventional flavoring, perfuming, or colouring agents.

Administration is also possible by subcutaneous injection, fluid unit dose forms being prepared containing a compound of the present invention and a sterile vehicle.

The choice of pre-estrogen(s) should be partly dictated by their ease of absorption through skin.

AROMATASE INHIBITORS (not a complete list)

Aminoglutethimide
4-OH androstenedione
6-hydroximino-androstenedione
9, 10-dimethyl 1,2-benzanthracene
1,4,6-androstatrien-3,17-dione
Atamestane
Exemstane
Fadrozole
Vorozole
1,2,4-triazole-3-alanine
Rogletimide In this context an inhibitor is any agent capable of preventing the aromatase enzyme from carrying out its normal function. This includes partial and full antagonists and also encompasses antibodies raised against at least a part of the aromatase enzyme. The antibodies may be polyclonal or monoclonal and can be produced using techniques well known to those skilled in the art. Manipulated forms of naturally occurring androgens may also be used.

CONCLUSIONS AND SUMMARY

Androgen hormones are necessary for the development of male balding but the mechanism of their action on scalp hair follicles has been obscure. We have proposed that balding is cause by estrogens which are synthesized locally in the scalp from circulating androgens (testosterone, androstenedione) by the action of the enzyme, aromatase. Estrogens are known to inhibit hair growth in other mammals. Also, aromatase activity is androgen dependent in some tissues, e.g., brain. To investigate this hypothesis we have studied aromatase in skin from balding and non-balding male scalp, female scalp and male beard (where androgens stimulate hair growth). These studies have used cultured skin fibroblasts, cultured hair follicle dermal papilla cells and skin tissue.

Results

Skin fibroblast lines from beard (n=5), occiptal scalp (n=5) and frontal scalp (n=7) all possessed aromatase activity. Enzyme kinetic values were established by incubating cells with the substrate (androstenedione) in a range of concentrations. The highest activities were found in cell lines from the frontal scalp, i.e, from a potentially balding site. Mean $V_{max}$ (fmol/mg protein/hour)+/− SEM in beard, occipital and frontal cells were 892+/−155,914+/−188 and 2817+/−866 respectively. There was no difference in the Km for androstenedione (mean=25 nmol) between the three sites. This value is similar to that quoted for other tissues.

Fibroblast aromatase was stimulated by pre-incubating the cells with testosterone at a physiological concentration (10 nmol). 19 cell lines were studied. Mean fold increase in aromatase activity (+/− SEM) was 2.69+/−0.38 (p<0.02 paired t test). In separate experiments on three cell lines the response to a range of concentrations of testosterone and DHT was studied. Testosterone gave a 2 fold increase in aromatase maximal at 10 nmol. At the same concentration the response to DHT was over twice as great (4.3 fold). This response to testosterone and DHT was inhibited by cyproterone acetate (which blocks androgen receptors) indicating that androgen stimulation of skin aromatase is via an androgen receptor dependent mechanism.

No aromatase was detected in hair follicle dermal papilla cells cultured from any of the above sites (14 cell lines). Testosterone failed to induce aromatase in dermal papilla cells.

Dexamethasone stimulated aromatase 10–20 fold in fibroblasts (6 cell lines) and induced aromatase in dermal papilla cells (4 cell lines).

Fibroblast aromatase was inhibited by 4OH-androstenedione, a known inhibitor of aromatase in other tissues. Kinetic studies in 3 cell lines were consistent with irreversible competitive inhibition. 50% inhibition occurred at approximately 25 nmol concentration.

Aromatase mRNA was detected in skin fibroblasts (four cell lines) by the polymerase chain reaction (PCR). In spite of the absence of measurable enzyme activity we also detected aromatase mRNA in dermal papilla cells (four cell lines). Using a semi-quantitative dilutional technique the level of expression appeared greater in skin fibroblasts than in dermal papilla cells suggesting that the difference in enzyme activity between the two cell types is determined at the transcriptional level. PCR is an unreliable method for quantifying mRNA and we cannot exclude the possibility of post-transcriptional regulation. However, in experiments in which skin fibroblasts were incubated with conditioned media from dermal papilla cell cultures or were co-cultured with dermal papilla cells we found no evidence that dermal papilla cells contain or release factors which inhibit aromatase.

To determine whether the results obtained using cell culture are representative of events occurring in vivo aromatase was measured by the tritiated water assay in skin samples from male and female scalp. Tissue was minced and then incubated with $1\beta^3H$-androstenedione together with a source of NADPH. Each assay was done in the presence and absence of an aromatase inhibitor (4OH-androstenedione). Placental tissue was used as a positive control. Aromatase was detected in 9 of 12 samples from male frontal scalp by in only one of 5 samples from female scalp. The difference was statistically significant ($p<0.01$).

| fmol/g | Mean | Median | SEM |
|---|---|---|---|
| Male scalp | 91.7 | 44.5 | 32.8 |
| Female scalp | 3.6 | 0 | 3.6 |

Mean aromatase activity was greater in balding (110.0 fmol/g tissue/hour n=8) than in non-balding scalp (55.0 fmol/g tissue/hour n=4) but the difference was not significant on this small number of samples. The addition of 25 nmol 4OH-androstenedione reduced activity to background levels.

Our results support the original hypothesis. Aromatase activity is present in male scalp but is barely detectable or absent in female scalp. The cell culture studies show that skin aromatase is androgen dependent and this may be the explanation for the higher level of activity in males.

We believe we now have enough information to justify a pilot trial of a topical aromatase inhibitor in the treatment of male balding. We would use 4OH-androstenedione as its biochemistry and toxicity are well characterised and it is already licensed for use in humans (in the treatment of breast cancer).

EXAMPLE 1

A typical formulation for a topical preparation containing an aromatase inhibitor is as follows:
5% Propylene glycol
10% Ethanol or Isopropyl alcohol
85% Water
0.2–10% w/v 4-OH androstenedione 4-OH Androstenedione is dissolved in ethanol or isopropyl alcohol and propylene glycol. This solution is then diluted with water with stirring to provide a lotion suitable for application to the scalp.

Commercially available preservatives, such as one of the hydroxybenzoates, may optionally be added to increase shelf life of the product.

REFERENCES

1. Hamilton J B: Male hormone is a prerequisite and an incitant in common baldness, Am J A nat 71: 451, 1942.
2. Ebling FJG: The hormonal control of hair growth In: Orfanos C E, Happle R (eds.): *Hair and Hair Diseases* Berlin, Springer-Verlag, pp 267–299, 1990.
3. Jahoda C A B, Oliver R F: The dermal papilla and the growth of hair, in Orfanos C E, Happle R (eds): *Hair and Hair Diseases*, Berline, Spring-Verlag, pp 19–44, 1990.
4. Messenger AG: Control of hair growth: an overview, J Invest Dermatol 101: 4s–9s, 1993.
5. Randall V A, Thornton M J, Messenger A G: Cultured dermal papilla cells from androgen-dependent human hair follicles (e.g. beard) contain more androgen receptors than those from non-balding areas of scalp. J Endocrinol 133: 141–147, 1992.
6. Choudry R, Hodgins M B, Van der Kwast T H, Brinkmann A O, Boersma W J A: Localization of androgen receptors in human skin by immunohistochemistry: implications for the hormonal regulation of hair growth, sebaceous glands and sweat glands. J Endocrinol 133: 467, 1992.
7. Itami S, Kurata S. Sonoda T. Takayasu S: Mechanism of action of androgen in dermal papilla cells. Ann NY Acad Sci 642: 385–395, 1991.
8. Mohn M P: The effects of different hormonal states on the growth of hair in rats, in Montagna W, Ellis R A (eds): *The Biology of Hair Growth*, New York, Academic Press, pp 335–398, 1958.
9. Schweikert H U, Milewich L, Wilson J D: Aromatization of androstenedione by isolated human hairs. J Clin Endocrinol Mtab 40: 413, 1975.
10. Sawawa M E, Penneys N S: Immunohistochemical distribution of aromatase and 3B-hydroxysteroid dehydrogenase in human hair follicle and sebaceous gland. J Cutan Pathol 19: 309, 1991.
11. Stillman S C, Evans B A J, Hughes I A: Androgen dependent stimulation of aromatase activity in genital skin fibroblasts from normals and patients with androgen insensitivity. Clin Endocrinol 35: 533–538, 1991.
12. Hutchinson J B: Aromatase: neuromodulator in the control of behaviour. J Steroid Biochem Molec Biol 44: 509, 1993.
13. Lephart E D, Simpson E R: Assay of aromatase activity. Methods in Enzymology 206: 477–483, 1991.
4. Simpson E, Lauber M. Demeter M et al: Regulation of expression of the genes encoding steroidogenic enzymes. J Steroid Biochem Molec Biol 40: 45–52, 1991.
5. Harada N: A unique aromatase (P-450arom) mRNA formed by alternative use of tissue-specific exons 1 in human skin fibroblasts. Biochem Biophys Res Comm 189: 1001–1007, 1992.

I claim:

1. A method for treating hair loss of a subject comprising administering to an area of the subject to be treated, a material selected from the group consisting of an aromatase inhibitor, a medicament thereof, and a cosmetic agent thereof, thereby treating hair loss of the subject.

2. The method according to claim 1 wherein the aromatase inhibitor is selected from the group consisting of aminoglutethimide, 4-OH androstenedione, 6-hydroximino-androstenedione, 9, 10-dimethyl 1,2-benzanthracene, 1,4,6-androstatrien-3,17-dione, atamestane, exemstane, fadrozole, vorozole, 1,2,4-triazole-3-alanine and rogletimide.

3. A method for reducing regression of hair growth comprising contacting an area of a subject with a material selected from the group consisting of an aromatase inhibitor, a medicament thereof, and a cosmetic agent thereof, so as to reduce the regression of hair growth in the area of the subject so contacted.

4. The method according to claim 3, wherein the aromatase inhibitor is selected form the group consisting of: aminoglutethimide, 4-OH androstenedione, 6-hydroximino-androstenedione, 9, 10-dimethyl 1,2-benzanthracene, 1,4,6-androstatrien-3,17-dione, atamestane, exemstane, fadrozole, vorozole, 1,2,4-triazole-3-alanine and rogletimide.

5. A medicament and/or cosmetic agent comprising an aromatase inhibitor and an androgen receptor antagonist.

6. The medicament and/or cosmetic agent as claimed in claim 5, wherein the aromatase inhibitor is selected form the group consisting of: aminoglutethimide, 4-OH androstenedione, 6-hydroximino-androstenedione, 9, 10-dimethyl 1,2-benzanthracene, 1,4,6-androstatrien-3,17-dione, atamestane, exemstane, fadrozole, vorozole, 1,2,4-triazole-3-alanine and rogletimide.

7. The medicament and/or cosmetic agent as claimed in claim 5, wherein the medicament and/or cosmetic agent is formulated for topical application with suitable excipients.

8. The medicament and/or cosmetic agent as claimed in claim 5, wherein the androgenic receptor antagonist is cyproterone acetate.

9. A method for treating hair loss of a subject comprising administering to an area of the subject to be treated an aromatase inhibitor, wherein said aromatase inhibitor comprises 4-OH androstenedione.

10. A method for reducing regression of hair growth comprising contacting an area of a subject with an aromatase inhibitor, which aromatase inhibitors comprises 4-OH androstenedione.

* * * * *